United States Patent
Koppinen et al.

(10) Patent No.: US 11,913,859 B2
(45) Date of Patent: Feb. 27, 2024

(54) TRAPPING AND RELEASING PARTICLES CARRIED BY GAS SAMPLE

(71) Applicant: Teknologian tutkimuskeskus VTT Oy, Espoo (FI)

(72) Inventors: Panu Koppinen, Espoo (FI); Teuvo Sillanpää, Espoo (FI); Markku Ylilammi, Espoo (FI)

(73) Assignee: Teknologian tutkimuskeskus VTT Oy, Espoo (FI)

(*) Notice: Subject to any disclaimer, the term of this patent is extended or adjusted under 35 U.S.C. 154(b) by 130 days.

(21) Appl. No.: 17/051,790

(22) PCT Filed: Apr. 15, 2019

(86) PCT No.: PCT/FI2019/050303
§ 371 (c)(1),
(2) Date: Oct. 30, 2020

(87) PCT Pub. No.: WO2019/211513
PCT Pub. Date: Nov. 7, 2019

(65) Prior Publication Data
US 2021/0116332 A1   Apr. 22, 2021

(30) Foreign Application Priority Data
Apr. 30, 2018 (FI) .................... 20185401

(51) Int. Cl.
*G01N 1/22* (2006.01)
*B01L 3/00* (2006.01)
(Continued)

(52) U.S. Cl.
CPC .......... *G01N 1/2202* (2013.01); *B01L 3/5027* (2013.01); *B01L 5/00* (2013.01);
(Continued)

(58) Field of Classification Search
CPC ............ B01L 3/5027; B01L 5/00; B06B 1/10; G01N 1/2202; G01N 1/2273;
(Continued)

(56) References Cited

U.S. PATENT DOCUMENTS

| 6,881,314 B1 | 4/2005 | Wang et al. |
| 2006/0037915 A1 | 2/2006 | Strand et al. |

(Continued)

FOREIGN PATENT DOCUMENTS

WO    WO2013172610 A1   11/2013

OTHER PUBLICATIONS

Zeshan et al., 2D CMUT Array Based Ultrasonic Micromanipulation Platform, 2016, IEEE International Ultrasonics Symposium Proceedings (Year: 2016).*

(Continued)

*Primary Examiner* — Christine T Mui
*Assistant Examiner* — Kathryn Elizabeth Limbaugh
(74) *Attorney, Agent, or Firm* — Laine IP Oy

(57) ABSTRACT

According to an example aspect of the present invention, there is provided an apparatus comprising a volume for receiving a gas sample; and an ultrasonic transducer; wherein the ultrasonic transducer is caused to generate a standing wave to the volume, said standing wave comprising at least one particle trapping zone for trapping particles carried by the gas sample, and to release particles trapped to the at least particle trapping zone by decreasing power of the standing wave to at least one lower power level and/or switching off the standing wave.

4 Claims, 3 Drawing Sheets

(51) Int. Cl.
  *B01L 5/00*    (2006.01)
  *B06B 1/10*    (2006.01)
  *G01N 1/40*    (2006.01)
  *G01N 15/00*   (2006.01)
  *G01N 15/06*   (2006.01)
  *G01N 33/00*   (2006.01)

(52) U.S. Cl.
  CPC ............ *B06B 1/10* (2013.01); *G01N 1/4077* (2013.01); *G01N 15/0656* (2013.01); *G01N 33/0004* (2013.01); *G01N 2001/4094* (2013.01); *G01N 2015/0053* (2013.01); *G01N 2015/0693* (2013.01)

(58) Field of Classification Search
  CPC ............ G01N 1/4077; G01N 15/0205; G01N 15/0266; G01N 15/0656; G01N 2001/4094; G01N 2015/0053; G01N 2015/0693; G01N 33/0004; G01N 2021/3181; G01N 2021/5957; G01N 2021/8887; G01N 21/314; G01N 21/3151; G01N 21/59; G01N 21/8851; G06N 20/00; G08C 17/02
  See application file for complete search history.

(56) References Cited

U.S. PATENT DOCUMENTS

2015/0107335 A1   4/2015  Meegan et al.
2016/0059206 A1*  3/2016  Chen .................... G01N 1/4077
                                                    422/127
2016/0231223 A1   8/2016  Wang et al.
2017/0369865 A1  12/2017  Lipkens et al.

OTHER PUBLICATIONS

Petersson et al., Separation of lipids from blood utilizing ultrasonic standing waves in microfluidic channels, Aug. 18, 2004, The Analyst, vol. 129, pp. 938-943 (Year: 2004).*
Jajarmi: Acoustic separation of submicron particles in gaseous flows. Teclmical Reports from Royal Institute of Technology KTH Mechanics, May 1, 2015.
Koppinen et al: A novel MEMS gas sensor based on ultrasonic resonance cavity. IEEE, IUS, Sep. 3-6, 2014, pp. 655-658.
Zeshan et al: 2D CMUT array based ultrasonic micromanipulation platform. IEEE, IUS, Nov. 3, 2016, vol. 1-4, ISSN 1948-5727.

* cited by examiner

TRAPPING AND RELEASING PARTICLES CARRIED BY GAS SAMPLE

FIELD

The present invention relates to trapping and releasing particles carried by a gas sample.

BACKGROUND

Poor air quality due to chemical and particulate pollutants is a serious health hazard in urban areas. According to World Health Organization (WHO) exposure to air pollution has been responsible for seven million deaths in 2012 (one in eight of total global deaths). In addition to the obvious effect of the air pollutants on respiratory system in humans, strong links between exposure to air pollution and, among many other medical conditions, cardiovascular diseases and cancer have been established. The health damage from the pollutants is manifold and depends on their composition and state (e.g., gaseous or solid). Monitoring of various air pollutants, their concentrations and space-time distribution is, therefore, important not only on the global scale, but on a finer grid within regions and localities for localization of the pollution sources and geographical extend of the pollution. In order to measure the transport of the pollutants and forecast the evolution of the pollution spread, the measurements need to be in real-time and preferably over a dense spatial grid.

Existing fine particle detection schemes are typically bulky and very expensive, whereby they are not suitable for sensor networks and personal use.

SUMMARY OF THE INVENTION

The invention is defined by the features of the independent claims. Some specific embodiments are defined in the dependent claims.

According to a first aspect of the present invention, there is provided an apparatus comprising: a volume for receiving a gas sample; and an ultrasonic transducer: wherein the ultrasonic transducer is caused to: generate a standing wave to the volume, said standing wave comprising at least one particle trapping zone for trapping particles carried by the gas sample; release particles trapped to the at least particle trapping zone by decreasing power of the standing wave to at least one lower power level and/or switching off the standing wave.

According to a second aspect of the present invention, there is provided a method comprising receiving a gas sample to a volume; generating by an ultrasonic transducer a standing wave to the volume, said standing wave comprising at least one particle trapping zone for trapping particles carried by the gas sample; releasing, by the ultrasonic transducer, particles trapped to the at least particle trapping zone by decreasing power of the standing wave to at least one lower power level, and/or switching off, by the ultrasonic transducer, the standing wave.

According to a third aspect of the present invention, there is provided a non-transitory computer readable medium having stored thereon a set of computer readable instructions that, when executed by at least one processor, cause an apparatus to at least: receiving a gas sample to a volume; generating by an ultrasonic transducer a standing wave to the volume, said standing wave comprising at least one particle trapping zone for trapping particles carried by the gas sample; releasing, by the ultrasonic transducer, particles trapped to the at least particle trapping zone by decreasing power of the standing wave to at least one lower power level, and/or switching off, by the ultrasonic transducer, the standing wave.

According to a fourth aspect of the present invention, there is provided a handheld communications device comprising an apparatus according to an aspect.

According to a fifth aspect of the present invention, there is provided a computer program configured to cause a method in accordance with an aspect, when the computer program is executed by at least one processor.

According to a sixth aspect of the present invention, there is provided an apparatus comprising at least one processing core, at least one memory including computer program code, the at least one memory and the computer program code being configured to, with the at least one processing core, cause the apparatus at least to: receiving a gas sample to a volume; generating by an ultrasonic transducer a standing wave to the volume, said standing wave comprising at least one particle trapping zone for trapping particles carried by the gas sample; releasing, by the ultrasonic transducer, particles trapped to the at least particle trapping zone by decreasing power of the standing wave to at least one lower power level, and/or switching off, by the ultrasonic transducer, the standing wave.

EMBODIMENTS

There is provided apparatus comprising a volume for receiving a gas sample and an ultrasonic transducer. The ultrasonic transducer is caused to generate a standing wave to the volume, said standing wave comprising at least one particle trapping zone for trapping particles carried by the gas sample, and release particles trapped to the at least particle trapping zone by decreasing power of the standing wave to at least one lower power level and/or switching off the standing wave. In this way access to particle size distribution manipulation may be provided.

Figure 1:
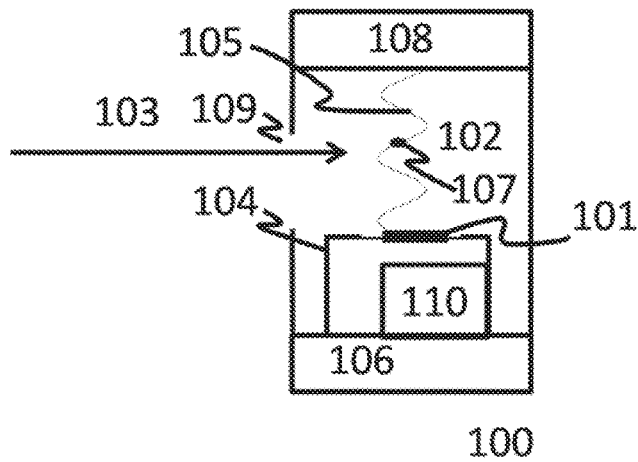
FIG. 1 illustrates an apparatus in accordance with at least some embodiments of the present invention.
Figure 2:
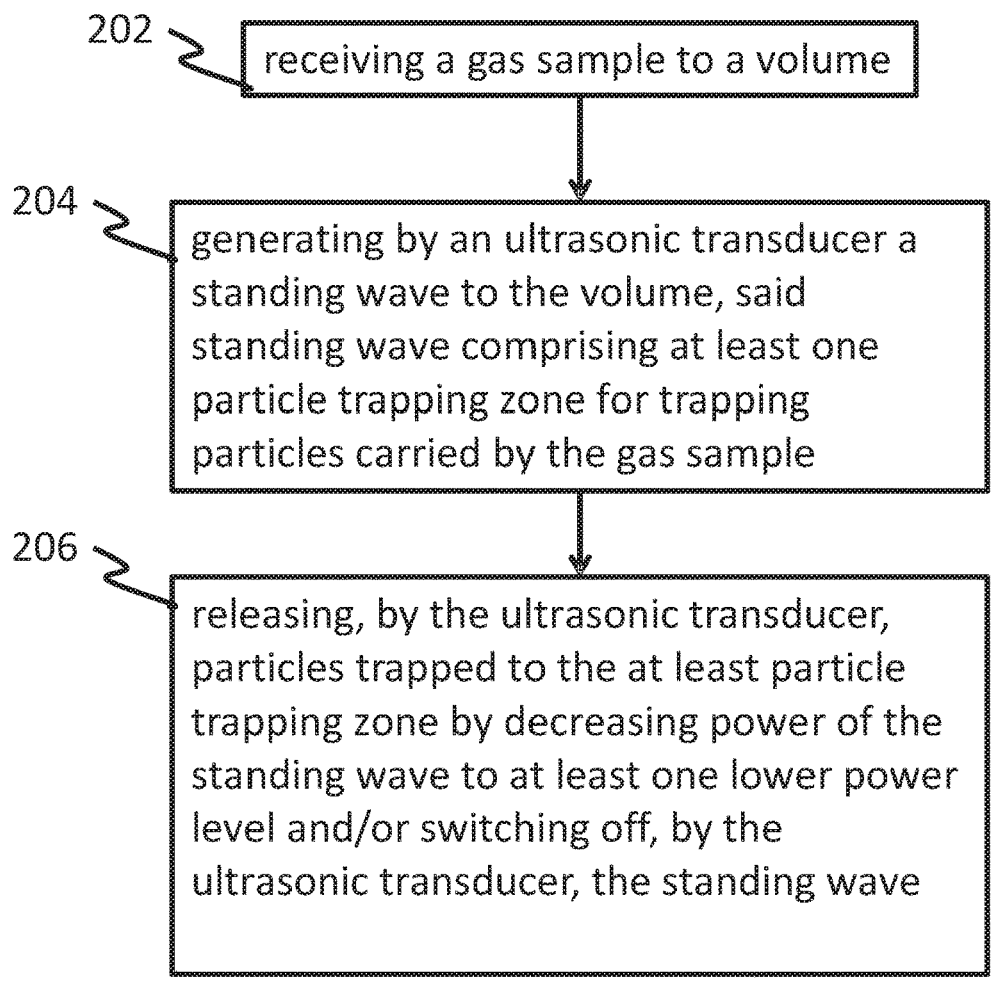
FIG. 2 illustrates a method in accordance with at least some embodiments of the present invention.

FIG. 1 illustrates an apparatus 100 in accordance with at least some embodiments of the present invention. The apparatus comprises a volume 102 for receiving a gas sample 103, and an ultrasonic transducer 104. The ultrasonic transducer is configured to generate a standing wave 105 to the volume. The standing wave comprises at least one particle trapping zone 107 for trapping particles carried by the gas sample. The ultrasonic transducer is further configured to release particles trapped to the at least particle trapping zone by decreasing power of the standing wave to at least one lower power level and/or switching off the standing wave. Particles carried by the gas sample are agglomerated, illustrated as black dot in FIG. 1, to the particle trapping zone of the standing wave due to acoustic trapping forces caused by pressure field of the sound wave.

The particles are controllably released from the particle trapping zone, whereby access to particle size distribution manipulation is provided. An example of an application area of the apparatus is trapping and releasing pollutants from the air.

In an example, the volume may be formed by walls 108 and the volume may be connected to its environment by one or more channels 109 that at least allow the gas sample to enter the volume.

It should be appreciated that the volume 102 may be acoustically damped from ambient sounds. The acoustical dampening may be provided by acoustically attenuating material of the walls and by acoustical dampeners positioned at the channels 109. The acoustical dampeners may be arranged to close the channels after the gas sample has been received to the volume.

The acoustical dampening provides that the volume is acoustically sealed from ambient sounds. In this way particles carried by the gas flow 103 into the volume may be trapped more efficiently to the particle trapping zone 107 such that the amount of untrapped particles may be small.

In an embodiment, the ultrasonic transducer 104 is a MEMS based ultrasonic transducer (MUT) or an array of MUTs, which may be, for example, CMUT (capacitive microelectromechanical ultrasonic transducer) or PMUT (capacitive microelectromechanical ultrasonic transducer) devices. The ultrasonic transducer may be provided on a silicon substrate 106, for example on a chip arranged on the silicon substrate. The MEMS based ultrasonic transducer provides that the overall size of the apparatus comprising the MUT or array of MUTs may be small such that the apparatus may be portable. The apparatus is therefore, sufficiently small to be utilized in particle sensors serving as personal dosimeters and carried by people. The CMUT provides a further benefit that the transducer device may be used as a pressure sensor. The additional pressure sensing functionality is beneficial for utilizing the apparatus in pollution mapping and forecasting for example in a sensor network.

In an embodiment, the standing wave 105 has a length of 100 μm to 10 μm. In this way the overall size of the apparatus may be small such that the apparatus may be portable. The apparatus is therefore, sufficiently small to be utilized in particle sensors that are personal dosimeters carried by people.

In an embodiment the particle trapping zone 107 comprises a location of the minimum or maximum velocity of gas molecules depending of the mass density of the particle material. Particles carried by the gas are agglomerated, illustrated as black dot in FIG. 1, to the particle trapping zone of the standing waves due to acoustic trapping forces caused by pressure field of the sound wave.

In an embodiment, the apparatus 100 comprises a particle detection area 101. In this way information indicating an amount of particles released from the particle trapping zone may be obtained. Particles released from the particle trapping zone may be carried to the particle detection area by a gas flow, gravity and/or thermophoresis. The method the released particles are carried to the particle detection area may depend on the implementation of the apparatus, for example the particle detection area used. The particle detection area may be based on mass of the particles, capacitive detection or optical detection. In an example the particle detection area may be arranged on one or more walls 108 or other surfaces forming the volume 102. In one example, the particle detection area may be provided on the ultrasonic transducer 104. The particle detection area may be configured to generate information indicating an amount of particles, for example a particle density [mg/m^3]. The information indicating an amount of particles may indicate an amount of a specific size or a size rage of particles. Sizes of particles may be defined by diameters of particles, for example 0.25, 0.5, 1, 2, 5 μm.

It should be appreciated that in accordance with at least some embodiments, the apparatus 100 comprises means for receiving a gas sample to a volume, generating by an ultrasonic transducer a standing wave to the volume, said standing wave comprising at least one particle trapping zone for trapping particles carried by the gas sample, releasing, by the ultrasonic transducer, particles trapped to the at least particle trapping zone by decreasing power of the standing wave to at least one lower power level, and/or switching off, by the ultrasonic transducer, the standing wave.

In an embodiment the apparatus 100 may comprise at least one processing core, at least one memory including computer program code, the at least one memory and the computer program code being configured to, with the at least one processing core, cause the apparatus at least to: receiving a gas sample to a volume; generating by an ultrasonic transducer a standing wave to the volume, said standing wave comprising at least one particle trapping zone for trapping particles carried by the gas sample; releasing, by the ultrasonic transducer, particles trapped to the at least particle trapping zone by decreasing power of the standing wave to at least one lower power level, and/or switching off, by the ultrasonic transducer, the standing wave.

In some embodiments the apparatus 100 may comprise a control device 110. The control device may be configured at least to obtain information indicating an amount of particles, for example a particle density [mg/m^3] from the particle detection area 101. The information indicating an amount of particles may comprise information indicating an amount of particles of a specific size or a size rage of particles generated by the particle detection area. The control device may be configured to control to cause one or more functionalities according to an embodiment. The control device may be configured to cause the ultrasonic transducer to cause the ultrasonic transducer to generate a standing wave, whereby the standing wave is switched on. The control device may be configured to set the power of the standing wave, and switch the standing wave on and off.

FIG. 2 illustrates a method in accordance with at least some embodiments of the present invention. The method provides way access to particle size distribution manipulation. The method may be performed by the apparatus described with FIG. 1.

Phase 202 receiving a gas sample to a volume. Phase 204 comprises generating by an ultrasonic transducer a standing wave to the volume, said standing wave comprising at least one particle trapping zone for trapping particles carried by the gas sample. In an example the gas sample may be received to the volume by a flow of gas through a channel. The flow of gas may be controlled by a fan arranged at the channel or the gas sample may flow freely into the volume. Phase 206 comprises releasing, by the ultrasonic transducer, particles trapped to the at least particle trapping zone by decreasing power of the standing wave to at least one lower power level and/or switching off, by the ultrasonic transducer, the standing wave.

FIG. 3 illustrates a method in accordance with at least some embodiments of the present invention. The method may be performed by the apparatus described with FIG. 1 for example. The method may be performed in connection with phase 206 of FIG. 2, for example.

Phase 302 may comprise controlling size of the released particles by the power level of the standing wave and/or a time the particle standing wave is switched off. In this way particles of specific size or a size range may be released from the particle trapping zone in a controlled manner such that a particle size distribution of the gas sample may be determined, by a particle detection area, based on arrival time distribution of the released particles.

In an example, controlling the time the standing wave is switched off comprises that the standing wave may be switched off for a time period such that particles may be released from the particle trapping zone. After the time period has passed, the standing wave may be switched on to prevent further particles to be released from the particle trapping zone. The time period the standing wave is switched off provides that particles of a specific size or a size range, for example having a diameter of 0.25, 0.5, 1, 2, 5 µm, may be released from the particle trapping zone, while particles that are not of the specific size or size range may remain trapped to the particle trapping zone. Accordingly, each size or size range of particles may have a corresponding time period that allows the particles to be released from the particle trapping zone.

In an example, controlling the power level of the standing wave comprises decreasing the power level of the standing wave to a lower power level to cause releasing particles from the particle trapping zone. The lower power level of the standing wave provides that particles of a specific size or a size range, for example having a diameter of 0.25, 0.5, 1, 2, 5 µm, may be released from the particle trapping zone, while particles that are not of the specific size or size range remain trapped to the particle trapping zone. The lower power level may be regarded lower compared to a current power level of the standing wave. Accordingly, each size or size range of particles may have a corresponding power level of the standing wave which that allows the particles to be released from the particle trapping zone. An initial power level of the standing wave may be determined such that particle sizes of interest may be trapped to the particle trapping zone.

Phase 304 may comprise detecting, by a particle detection area, particles released from the particle trapping zone. The particle detection area may be configured to generate information indicating an amount of particles, for example a particle density [mg/m^3]. The particle detection area may be based on mass of the particles, capacitive detection or optical detection.

Phase 306 may comprise determining, whether further particles are to be detected. Further particles are detected for example, if particles of interest, for example, a specific size or size range of particles are trapped in the particles trapping zone. Particles of interest may be determined to be trapped to the particle trapping zone on the basis of information indicating an amount of particles of a specific size or a size rage of particles generated by the particle detection area. For example, if particle detection area has generated information indicating amounts of particles having diameters 5 and 2 μm, it may be determined that particles having a smaller diameter have not yet been released, and further particles are to be detected.

If it is determined in phase 306 that further particles are to be detected, the method may proceed to phase 308 comprising adjusting the time the standing wave is switched off and/or the power level of the standing wave to a lower power level. The power of the standing wave may be adjusted to a power level causing a release of a specific size or a size range of particles from the particle trapping zone. The time the standing wave is switched off may be adjusted to a time period causing a release of a specific size or a size range of particles from the particle trapping zone. The particles may have a diameter of 0.25, 0.5, 1, 2, 5 μm, for example. After the power level and/or the time the standing wave is switched off have been adjusted the size of the released particles may be controlled using the adjusted power level and/or time in phase 302.

In an example, execution of phase 308 one or more times in the method after the detection is determined to be continued in phase 306, may comprise that the power of the standing wave may be decreased to lower power levels in a descending order of the power levels, whereby at each power level, a portion of the particles trapped to the particle trapping zone are released. The standing wave may be maintained at each power level for a time that is sufficient to allow detection of the released particles before further particles are released using an adjusted power level determined by phase 308. The portion of particles released may correspond to a specific size or a size range, for example particles having a diameter of 0.25, 0.5, 1, 2, 5 μm.

In an example, execution of phase 308 one or more times in the method after the detection is determined to be continued in phase 306, may comprise that the time the standing wave is switched off may be increased to time periods in an ascending order of the time periods. Accordingly, during each time period during which the standing wave is switched off, a portion of the particles trapped to the particle trapping zone are released. It should be appreciated that the standing wave should be switched on between the time periods the standing wave is switched off such that detection of the released particles is allowed before further particles are released. The portion of particles released may correspond to a specific size or a size range, for example particles having a diameter of 0.25, 0.5, 1, 2, 5 μm.

In an embodiment, phase 304 may comprise determining, by a particle detection area, a particle size distribution of the gas sample on the basis of arrival time distribution of the released particles. In this way the particle content of the gas sample may be analysed for determining concentrations of specific particles. The specific particles may be pollutants or other particles of interest in the gas sample. The particle size distribution may be obtained by detecting particles released from the particle trapping zone in phase 304 based on released particles of specific size or size ranges as controlled by the power level of the standing wave and/or the time the standing wave is switched off.

If it is determined in phase 306 that further particles are not to be detected, the method may end in 310. The method may not to be detected for example, if there are no particles of interest in the trapping zone.

FIG. 4 illustrates an example apparatus capable of supporting at least some embodiments of the present invention. Illustrated is device 400, which may comprise, for example, a control device 110 of FIG. 1. Comprised in device 400 is processor 410, which may comprise, for example, a single- or multi-core processor wherein a single-core processor comprises one processing core and a multi-core processor comprises more than one processing core. Processor 410 may comprise, in general, a control device. Processor 410 may comprise more than one processor. Processor 410 may be a control device. A processing core may comprise, for example, a Cortex-A8 processing core manufactured by ARM Holdings or a Steamroller processing core produced by Advanced Micro Devices Corporation. Processor 410 may comprise at least one Qualcomm Snapdragon and/or Intel Atom processor. Processor 410 may comprise at least one application-specific integrated circuit, ASIC. Processor

410 may comprise at least one field-programmable gate array, FPGA. Processor 410 may be means for performing method steps in device 400. Processor 410 may be configured, at least in part by computer instructions, to perform actions.

Device 400 may comprise memory 420. Memory 420 may comprise random-access memory and/or permanent memory. Memory 420 may comprise at least one RAM chip. Memory 420 may comprise solid-state, magnetic, optical and/or holographic memory, for example. Memory 420 may be at least in part accessible to processor 410. Memory 420 may be at least in part comprised in processor 410. Memory 420 may be means for storing information. Memory 420 may comprise computer instructions that processor 410 is configured to execute. When computer instructions configured to cause processor 410 to perform certain actions are stored in memory 420, and device 400 overall is configured to run under the direction of processor 410 using computer instructions from memory 420, processor 410 and/or its at least one processing core may be considered to be configured to perform said certain actions. Memory 420 may be at least in part comprised in processor 410. Memory 420 may be at least in part external to device 400 but accessible to device 400.

Device 400 may comprise a transmitter 430. Device 400 may comprise a receiver 440. Transmitter 430 and receiver 440 may be configured to transmit and receive, respectively, information in accordance with at least one cellular or non-cellular standard. Transmitter 430 may comprise more than one transmitter. Receiver 440 may comprise more than one receiver. Transmitter 430 and/or receiver 440 may be configured to operate in accordance with global system for mobile communication, GSM, wideband code division multiple access, WCDMA, 5G, long term evolution, LTE, IS-95, wireless local area network, WLAN, Ethernet and/or worldwide interoperability for microwave access, WiMAX, standards, for example.

Device 400 may comprise user interface, UI, 460. UI 460 may comprise at least one of a display, a keyboard, a touchscreen, a vibrator arranged to signal to a user by causing device 400 to vibrate, a speaker and a microphone. A user may be able to operate device 400 via UI 460, for example to configure particle detection measurements.

Processor 410 may be furnished with a transmitter arranged to output information from processor 410, via electrical leads internal to device 400, to other devices comprised in device 400. Such a transmitter may comprise a serial bus transmitter arranged to, for example, output information via at least one electrical lead to memory 420 for storage therein. Alternatively to a serial bus, the transmitter may comprise a parallel bus transmitter. Likewise processor 410 may comprise a receiver arranged to receive information in processor 410, via electrical leads internal to device 400, from other devices comprised in device 400. Such a receiver may comprise a serial bus receiver arranged to, for example, receive information via at least one electrical lead from receiver 440 for processing in processor 410. Alternatively to a serial bus, the receiver may comprise a parallel bus receiver.

Figure 4:
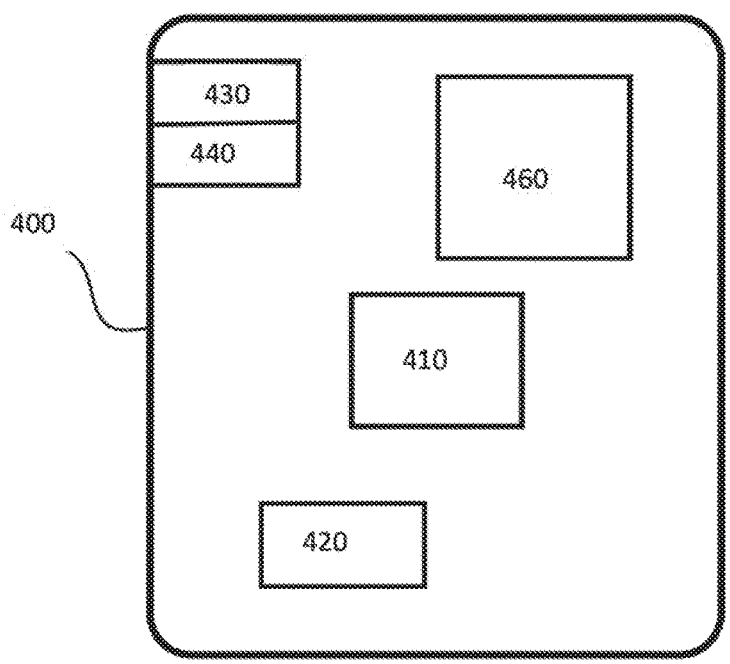
FIG. 4 illustrates an example apparatus capable of supporting at least some embodiments of the present invention.

Device 400 may comprise further devices not illustrated in FIG. 4. For example, where device 400 comprises a handheld communications device for example a smartphone, it may comprise at least one digital camera. Some devices 400 may comprise a back-facing camera and a front-facing camera, wherein the back-facing camera may be intended for digital photography and the front-facing camera for video telephony. Device 400 may comprise a fingerprint sensor arranged to authenticate, at least in part, a user of device 400. In some embodiments, device 400 lacks at least one device described above.

Processor 410, memory 420, transmitter 430, receiver 440 and/or UI 460 may be interconnected by electrical leads internal to device 400 in a multitude of different ways. For example, each of the aforementioned devices may be separately connected to a master bus internal to device 400, to allow for the devices to exchange information. However, as the skilled person will appreciate, this is only one example and depending on the embodiment various ways of interconnecting at least two of the aforementioned devices may be selected without departing from the scope of the present invention.

Figure 5:
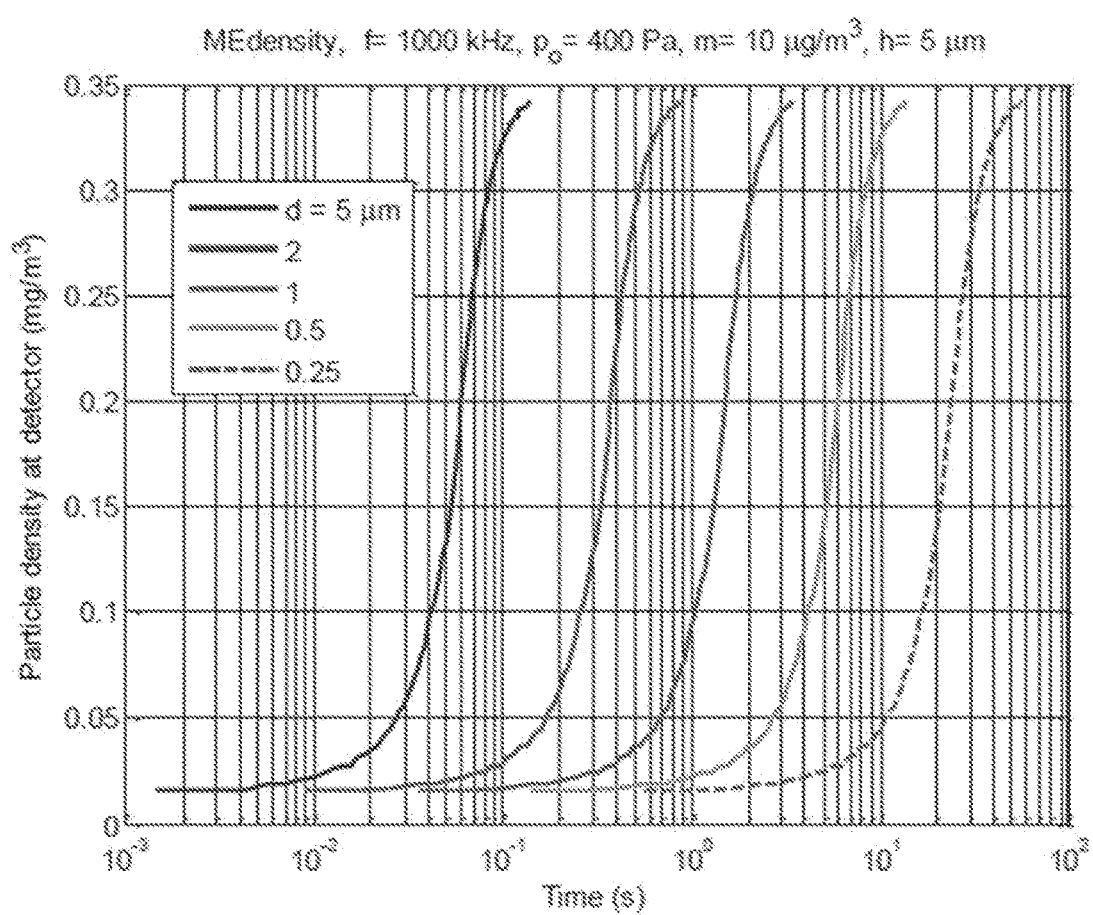
FIG. 5 illustrates a plot in accordance with at least some embodiments of the present invention.

FIG. 5 illustrates a plot in accordance with at least some embodiments of the present invention. In the plot, a particle density [mg/m^3] at a detection area is plotted against time [s]. The particle detection area may be in the apparatus described with FIG. 1. The plots illustrate detected particle densities of particle diameters of 5, 2, 1, 0.5 and 0.25 μm, when particles are released from a particle trapping zone in the order of their size starting from the largest particles. Thanks to releasing the particles by decreasing power of the standing wave to at least one lower power level and/or switching off the standing wave, the particles of diameters of 5, 2, 1, 0.5 and 0.25 μm arrive at the particle detection area at different times, and the arrival times are distributed and particle size distribution may be obtained.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

At least some embodiments of the present invention find industrial application in trapping and releasing particles.

ACRONYMS LIST

CMUT capacitive microelectromechanical ultrasonic transducer
MEMS microelectromechanical
MUT microelectromechanical ultrasonic transducer

REFERENCE SIGNS LIST

Figure 3:
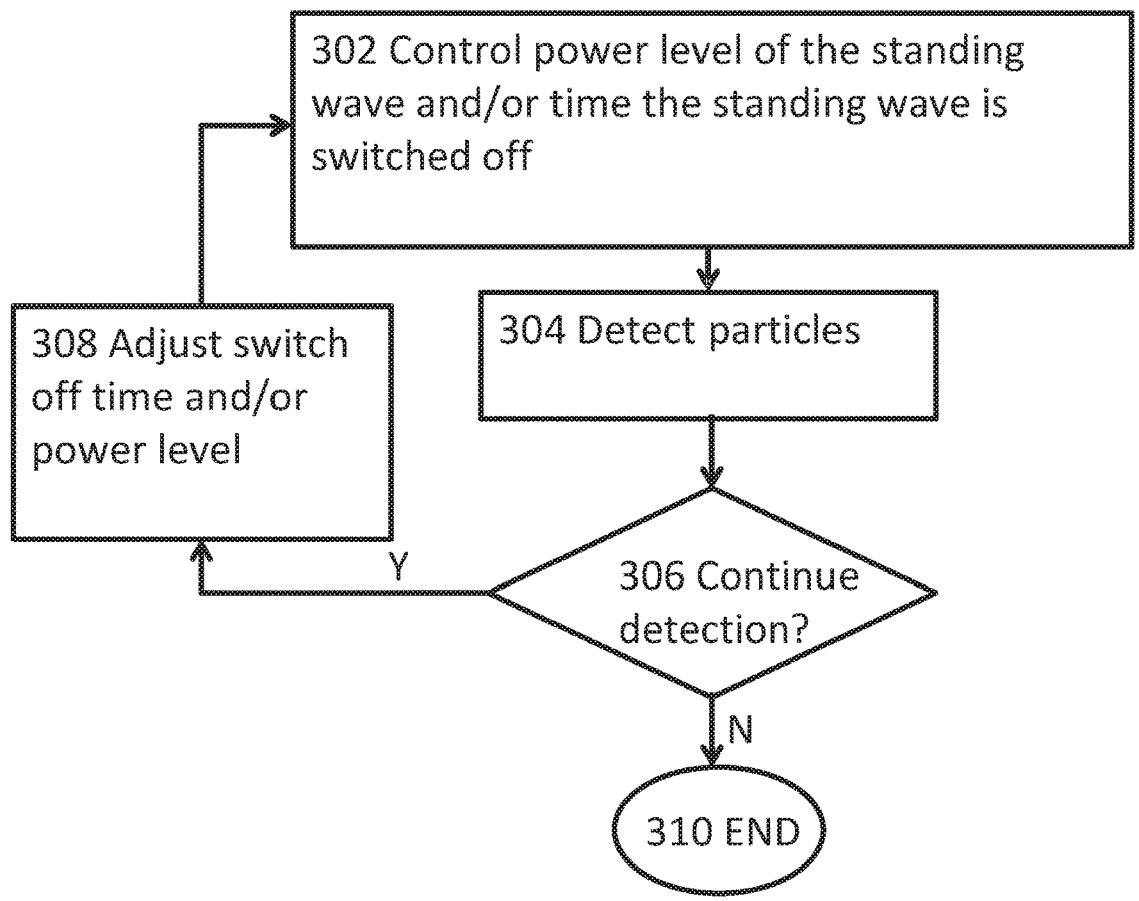
FIG. 3 illustrates a method in accordance with at least some embodiments of the present invention.

101 Particle detection area
102 Volume
103 Gas sample
104 Ultrasonic transducer 105 Standing wave
106 Silicon substrate
107 Particle trapping zone
108 Wall
109 Channel
110 Control device
202 to 206 Phases of FIG. 2
302 to 310 Phases of FIG. 3
400-460 Structure of the device of FIG. 4

The invention claimed is:

1. A method comprising:
receiving a gas sample to a volume of an on-chip fine particle sensor;
generating by a microelectromechanical, MEMS, ultrasonic transducer a standing wave to the volume, said standing wave comprising at least one particle trapping zone for trapping particles carried by the gas sample; an
releasing, by the MEMS ultrasonic transducer, particles trapped to the at least one particle trapping zone by decreasing power of the standing wave to at least one lower power level, and/or switching off, by the MEMS ultrasonic transducer, the standing wave, wherein size of the released particles is controlled by the power level of the standing wave and/or a time the at least one particle trapping zone is switched off to release plural sets of particles at different times, each set having particles of a same size range,
wherein the on-chip fine particle sensor is configured to determine a particle size distribution of the gas sample on the basis of an arrival time distribution of the released particles.

2. The method according to claim 1, further comprising detecting particles released from the at least one particle trapping zone by a particle detection area.

3. The method according to claim 1, wherein the power of the standing wave is adjusted to power level causing a release of a specific size or a size range of particles from the at least one particle trapping zone and/or the time the standing wave is switched off is adjusted to a time period causing a release of a specific size or a size range of particles from the at least one particle trapping zone.

4. A non-transitory computer readable medium having stored thereon a set of computer readable instructions that, when executed by at least one processor, cause an apparatus to at least:
receive a gas sample to a volume of an on-chip fine particle sensor;
generate by a microelectromechanical, MEMS, ultrasonic transducer a standing wave to the volume, said standing wave comprising at least one particle trapping zone for trapping particles carried by the gas sample; and
release, by the MEMS ultrasonic transducer, particles trapped to the at least one particle trapping zone by decreasing power of the standing wave to at least one lower power level, and/or switching off, by the MEMS ultrasonic transducer, the standing wave, wherein size of the released particles is controlled by the power level of the standing wave and/or a time the at least one particle trapping zone is switched off to release plural sets of particles at different times, each set having particles of a same size range,
wherein the on-chip fine particle sensor apparatus is configured to determine a particle size distribution of the gas sample on the basis of an arrival time distribution of the released particles.

* * * * *